US006689141B2

United States Patent
Ferrera et al.

(10) Patent No.: US 6,689,141 B2
(45) Date of Patent: Feb. 10, 2004

(54) MECHANISM FOR THE DEPLOYMENT OF ENDOVASCULAR IMPLANTS

(75) Inventors: David A. Ferrera, Manhattan Beach, CA (US); George R. Greene, Jr., Costa Mesa, CA (US); Brian J. Cox, Laguna Niguel, CA (US); Robert F. Rosenbluth, Laguna Niguel, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 84 days.

(21) Appl. No.: 10/143,724

(22) Filed: May 10, 2002

(65) Prior Publication Data

US 2002/0188311 A1 Dec. 12, 2002

Related U.S. Application Data

(63) Continuation-in-part of application No. 09/692,248, filed on Oct. 18, 2000, now Pat. No. 6,607,538.

(51) Int. Cl.⁷ .................................. A61F 11/00
(52) U.S. Cl. ........................ 606/108; 606/194
(58) Field of Search .................. 606/108, 151, 606/191, 194, 198, 200, 213; 623/1.12; 604/286, 104, 527, 93.01

(56) References Cited

U.S. PATENT DOCUMENTS

| 4,551,132 A | 11/1985 | Pasztor et al. |
| 4,795,741 A | 1/1989 | Leshchiner et al. |
| 4,819,637 A | 4/1989 | Dormandy, Jr. et al. |

(List continued on next page.)

FOREIGN PATENT DOCUMENTS

| EP | 0 941 703 A1 | 9/1999 |
| EP | 0 941 704 A1 | 9/1999 |
| EP | 1 010 396 A1 | 6/2000 |
| WO | WO 99/06097 | 2/1999 ...... A61M/29/00 |
| WO | WO 00/21443 | 4/2000 |

OTHER PUBLICATIONS

Rosenthal, D. et al.; "Angioscope–assisted endovascualr. . . " Cardiovascualr Surgery Jun. 1993 vol.1 No.3.
Rosenthal, David et al.; "Endovascular infrainguinal in situ . . . " Journal pof Vascualr Surgery pp. 453–458.

*Primary Examiner*—Manuel Mendez
*Assistant Examiner*—Mark K. Han
(74) *Attorney, Agent, or Firm*—Klein, O'Neil & Singh, LLP

(57) ABSTRACT

A mechanism for the deployment of a filamentous endovascular device includes a flexible deployment tube having an open proximal end, and a coupling element attached to the proximal end of the endovascular device. The deployment tube includes a distal section terminating in an open distal end, with a lumen defined between the proximal and distal ends. A retention sleeve is fixed around the distal section and includes a distal extension extending a short distance past the distal end of the deployment tube. The endovascular device is attached to the distal end of the deployment tube by fixing the retention sleeve around the coupling element, so that the coupling element is releasably held within the distal extension of the deployment tube. In use, the deployment tube, with the implant attached to its distal end, is passed intravascularly through a microcatheter to a target vascular site until the endovascular device is located within the site. To detach the endovascular device from the deployment tube, a liquid is injected through the lumen of the deployment tube so as to apply pressure to the upstream side of the coupling element, which is thus pushed out of the retention sleeve by the fluid pressure. The coupling element may include an internal or peripheral purge passage that allows air to be purged from the microcatheter prior to the intravascular passage of the endovascular device.

20 Claims, 11 Drawing Sheets

U.S. PATENT DOCUMENTS

| | | |
|---|---|---|
| 4,994,069 A | 2/1991 | Ritchart et al. |
| 5,001,009 A | 3/1991 | Whitbourne |
| 5,108,407 A | 4/1992 | Geremia et al. |
| 5,133,731 A | 7/1992 | Butler et al. |
| 5,167,624 A | 12/1992 | Butler et al. |
| 5,226,911 A | 7/1993 | Chee et al. |
| 5,312,415 A | 5/1994 | Palermo |
| 5,350,397 A | 9/1994 | Palermo et al. |
| 5,382,259 A | 1/1995 | Phelps et al. |
| 5,382,260 A | 1/1995 | Dormandy, Jr. et al. |
| 5,476,472 A | 12/1995 | Dormandy, Jr. et al. |
| 5,525,334 A | 6/1996 | Ito et al. |
| 5,578,074 A | 11/1996 | Mirigian |
| 5,580,568 A | 12/1996 | Greff et al. |
| 5,582,619 A | 12/1996 | Ken |
| 5,609,608 A | 3/1997 | Benett et al. |
| 5,624,461 A | 4/1997 | Mariant |
| 5,645,558 A | 7/1997 | Horton |
| 5,658,308 A | 8/1997 | Snyder |
| 5,718,711 A | 2/1998 | Berenstein et al. |
| 5,750,585 A | 5/1998 | Park et al. |
| 5,814,062 A | 9/1998 | Sepetka et al. |
| 5,823,198 A | 10/1998 | Jones et al. |
| 5,891,130 A | 4/1999 | Palermo et al. |
| 5,911,737 A | 6/1999 | Lee et al. |
| 6,015,424 A | 1/2000 | Rosenbluth et al. |
| 6,048,338 A | 4/2000 | Larson et al. |
| 6,056,759 A | 5/2000 | Fiedler |
| 6,063,100 A | 5/2000 | Diaz et al. |
| 6,068,644 A | 5/2000 | Lulo et al. |
| 6,083,220 A | 7/2000 | Guglielmi et al. |
| 6,102,932 A | 8/2000 | Kurz |
| 6,117,142 A | 9/2000 | Goodson et al. |
| 6,319,267 B1 | 11/2001 | Kurz |
| 6,361,547 B1 | 3/2002 | Hieshima |
| 6,440,098 B1 | 8/2002 | Luscher |
| 6,494,884 B2 | 12/2002 | Gifford, III et al. |
| 6,514,264 B1 | 2/2003 | Naglreiter |
| 6,544,225 B1 | 4/2003 | Lulo et al. |
| 6,554,849 B1 | 4/2003 | Jones et al. |

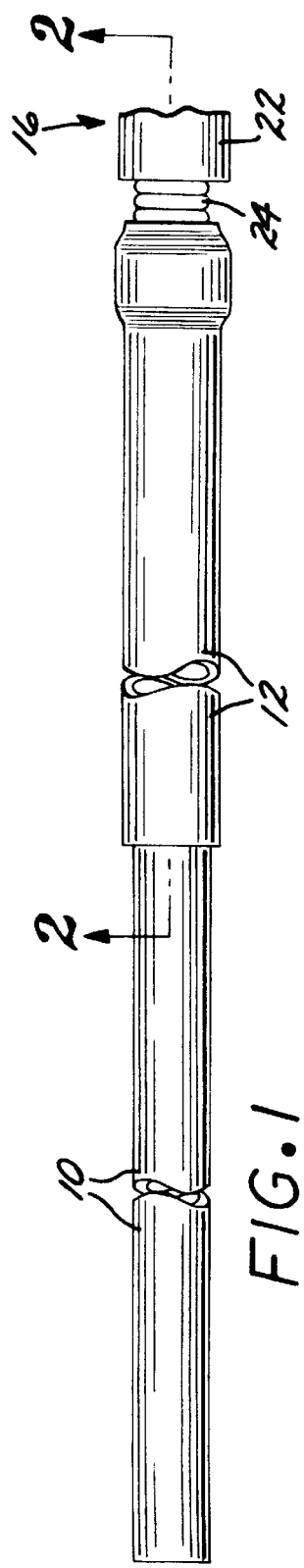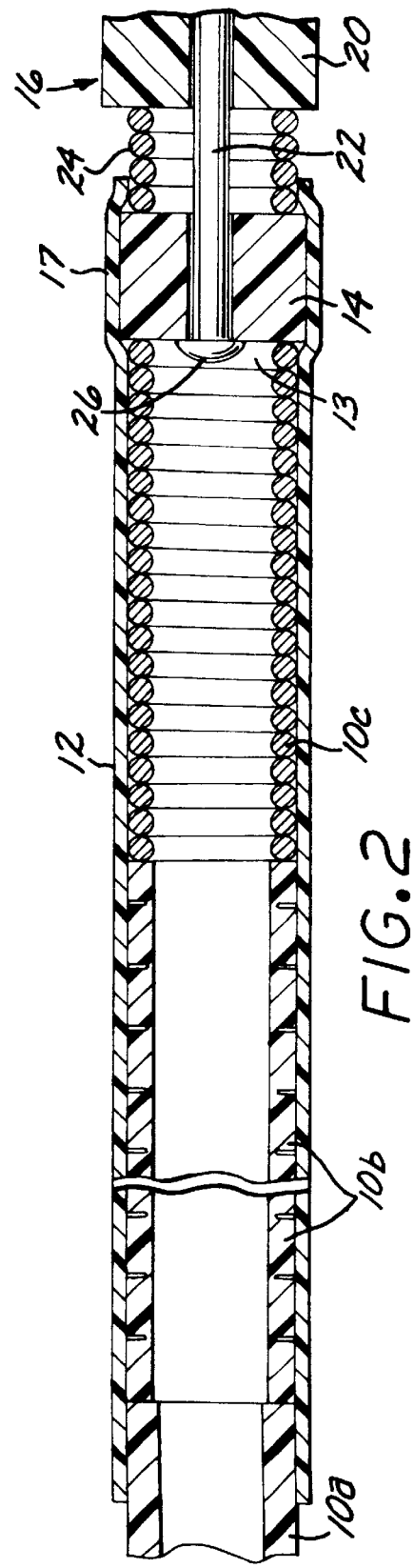

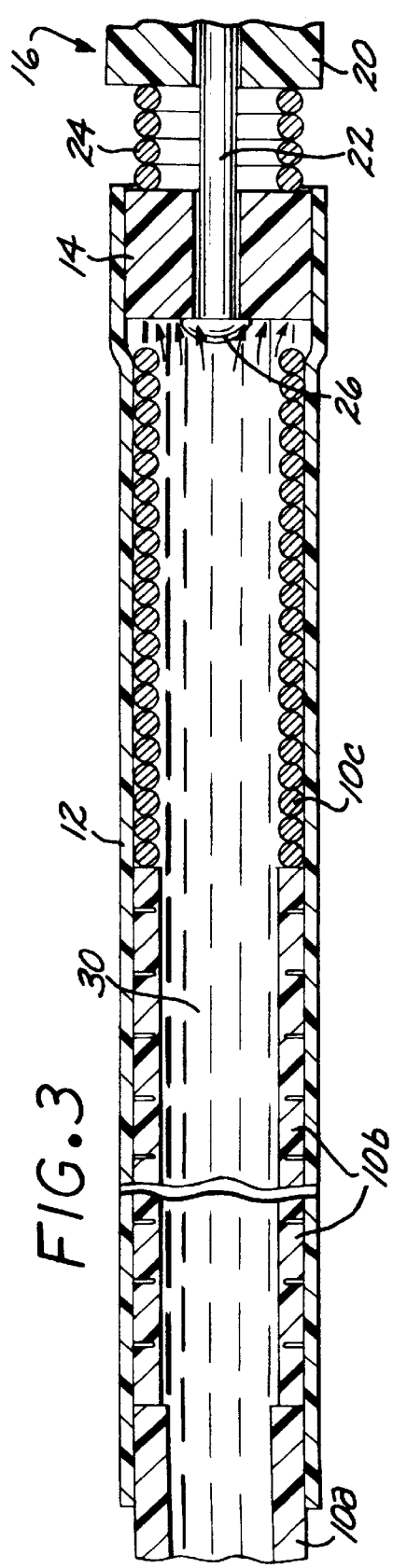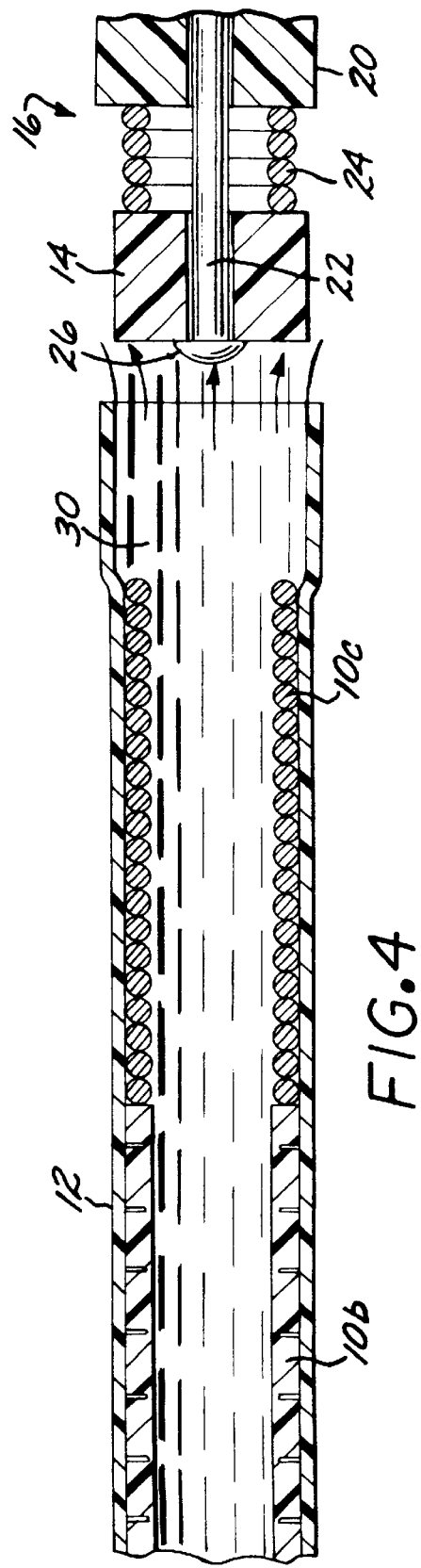

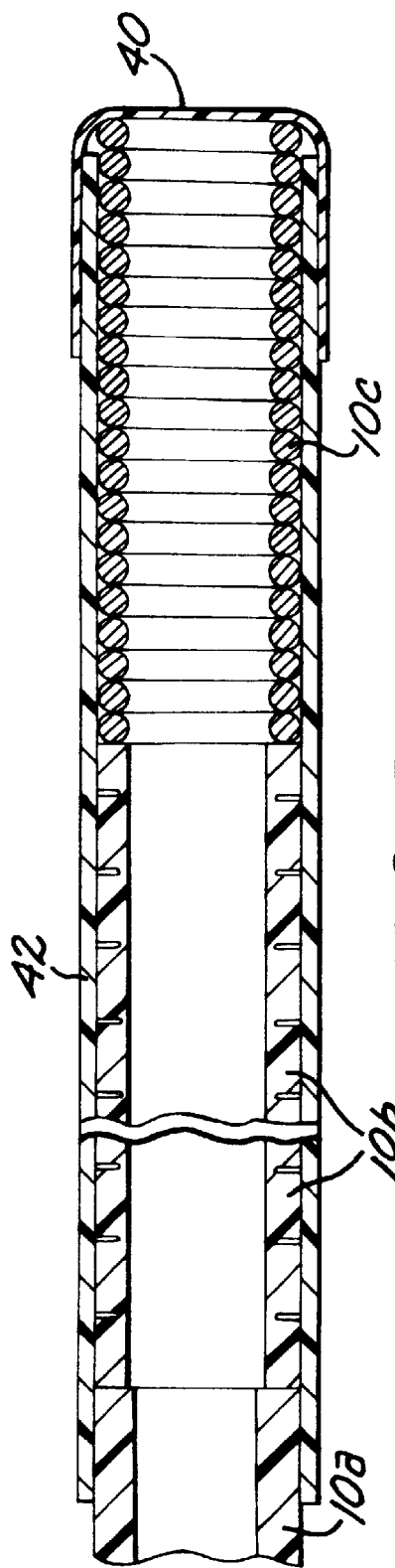
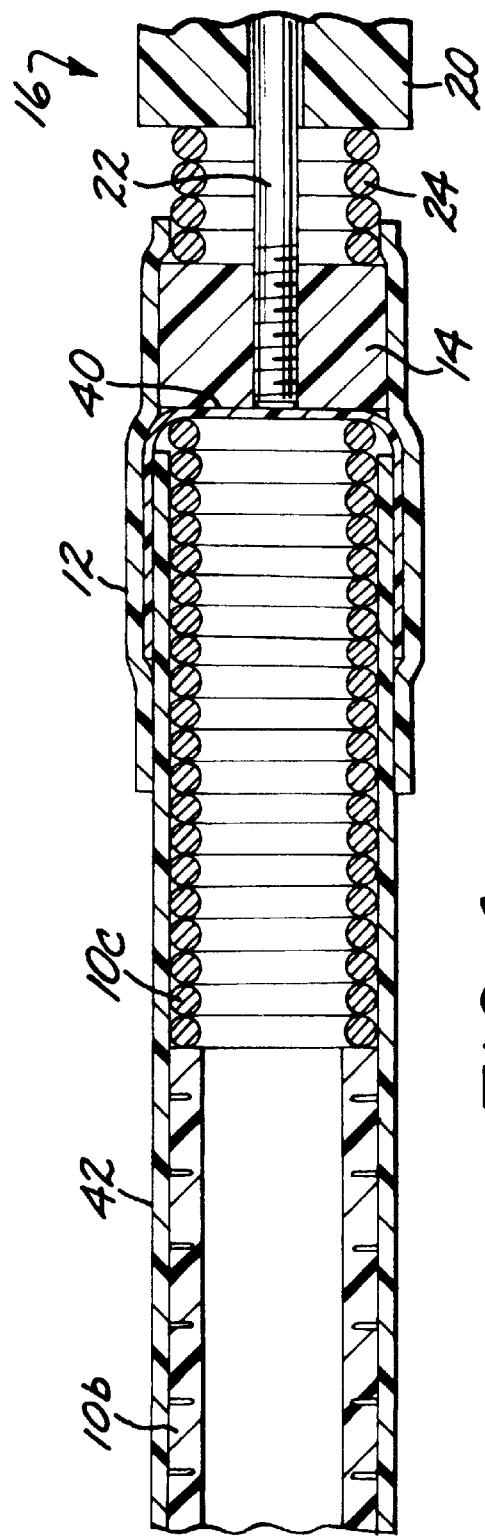

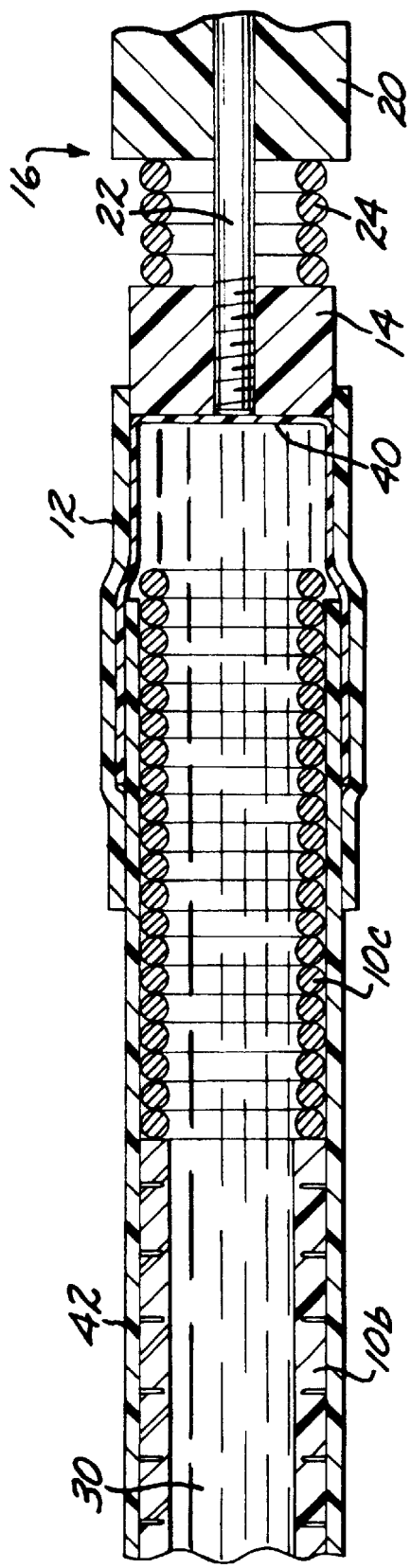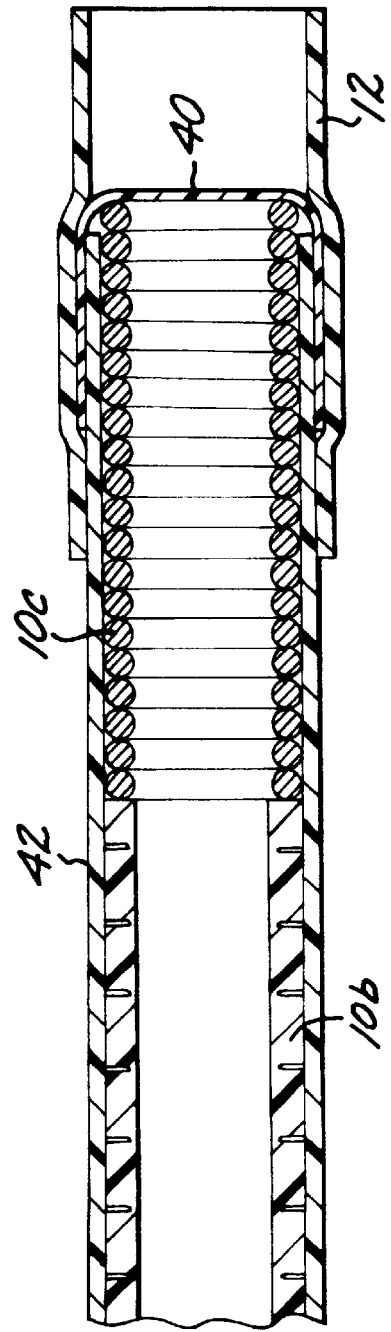

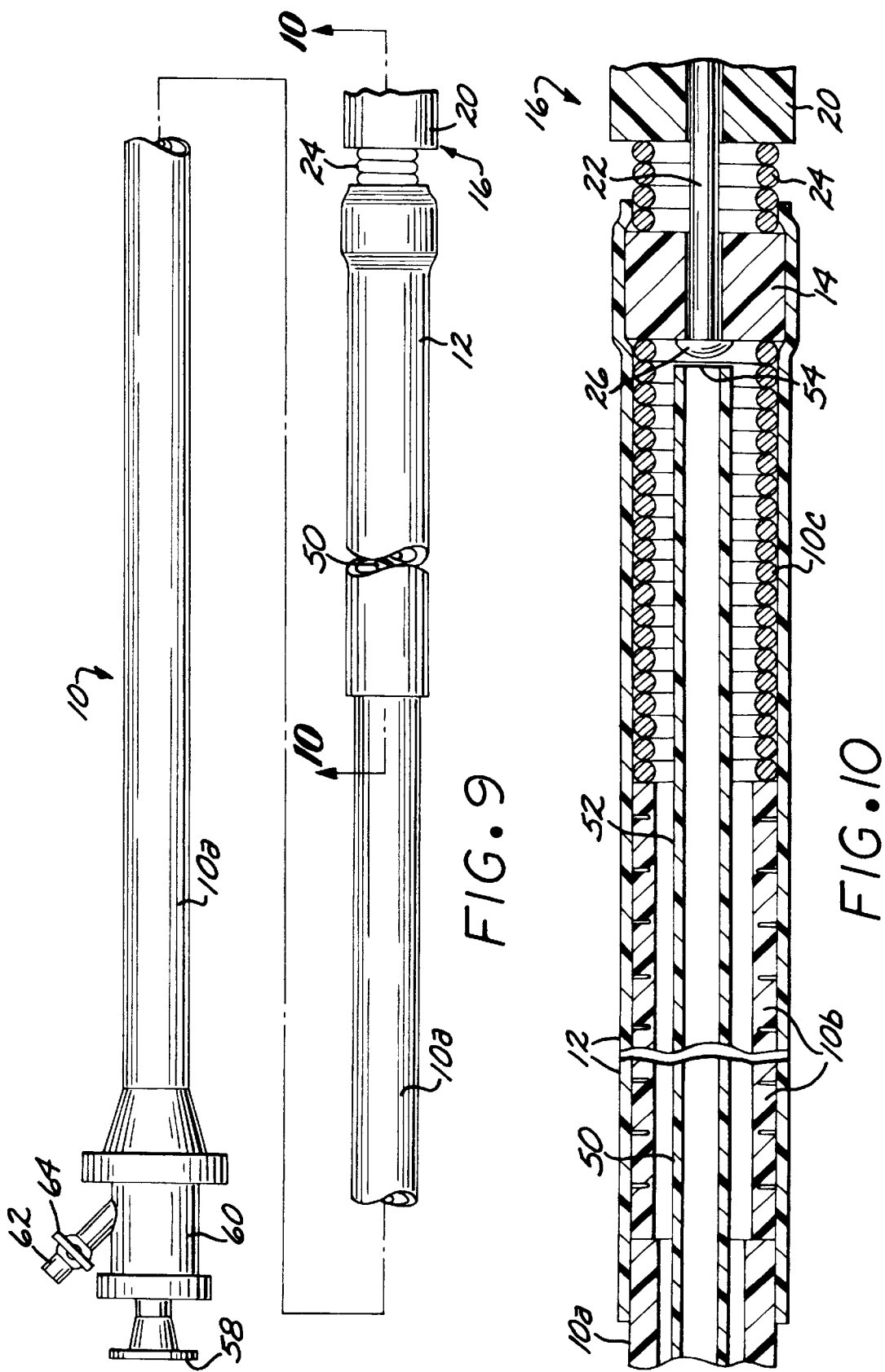

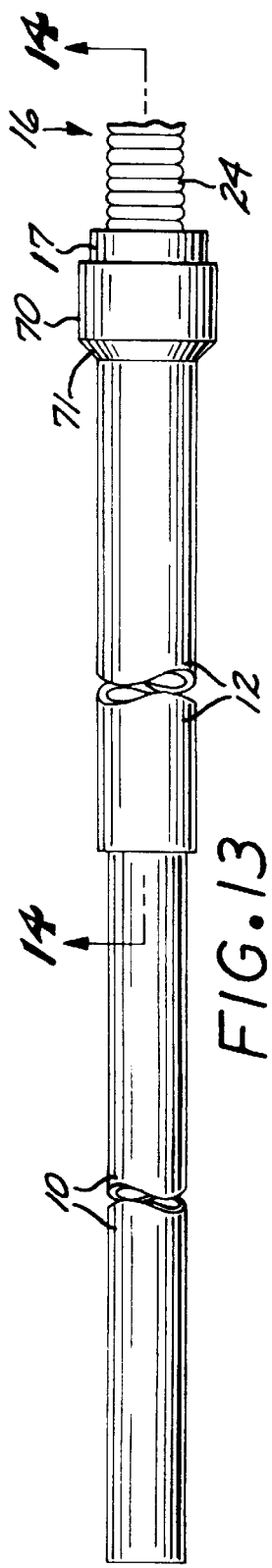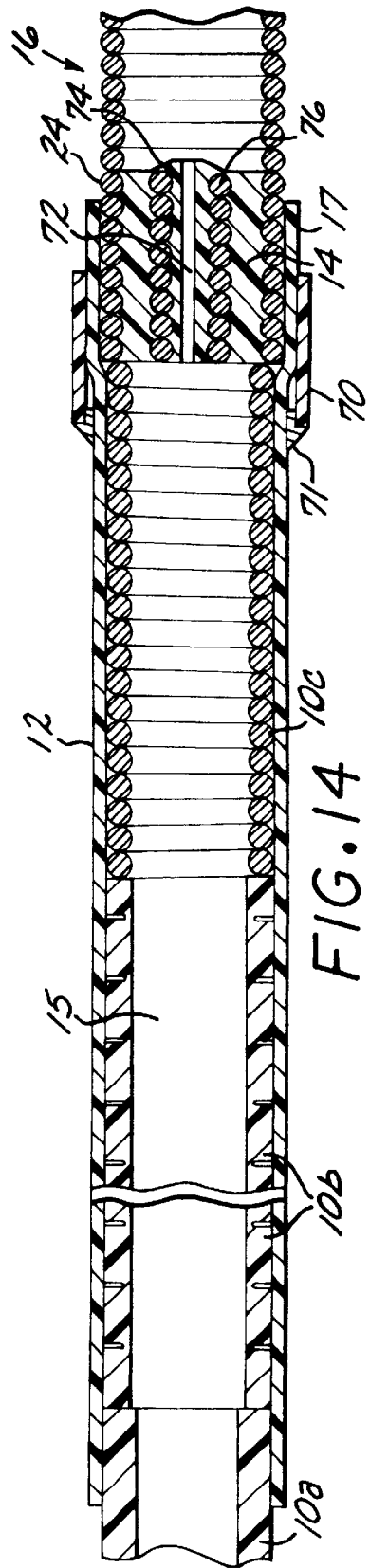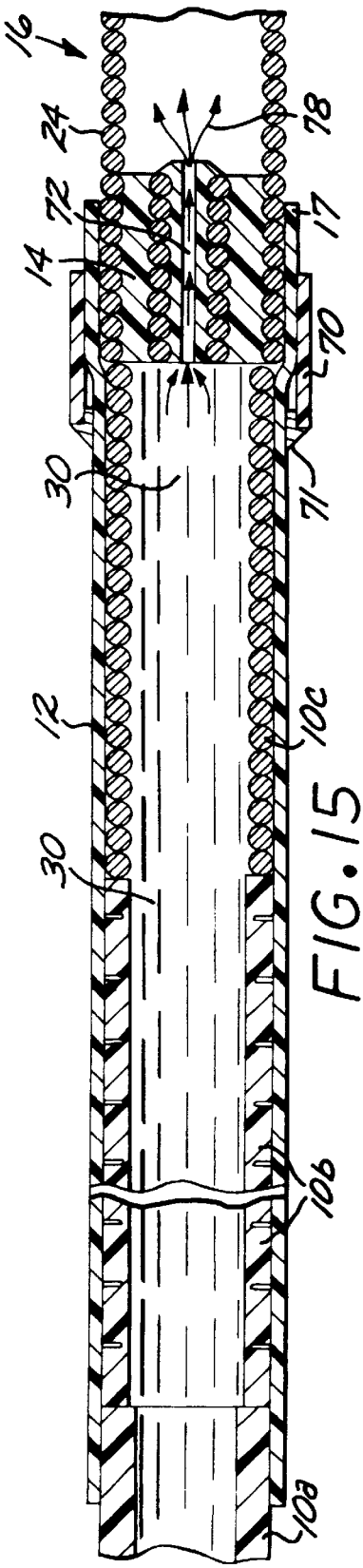

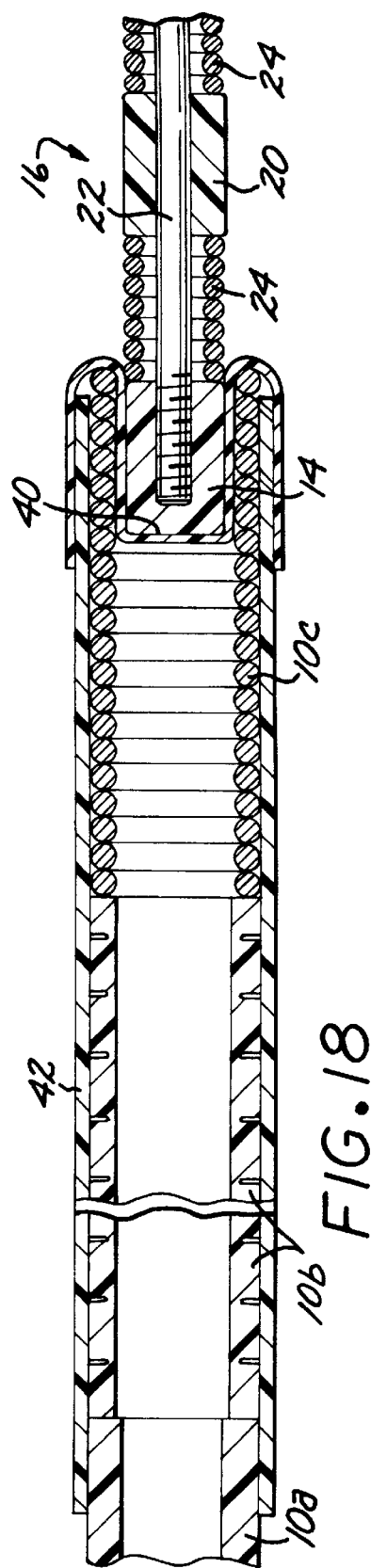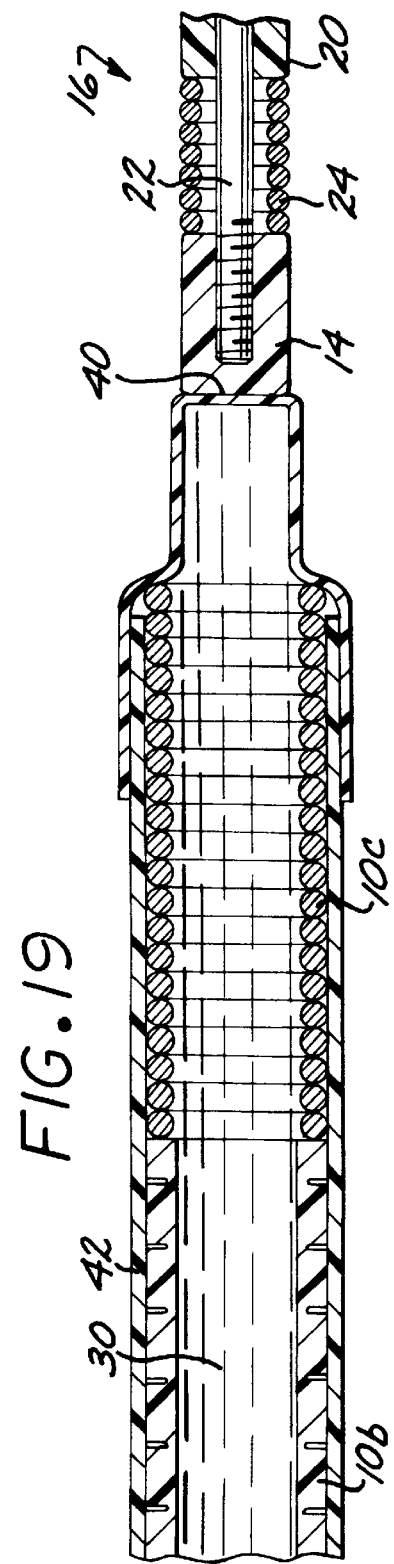

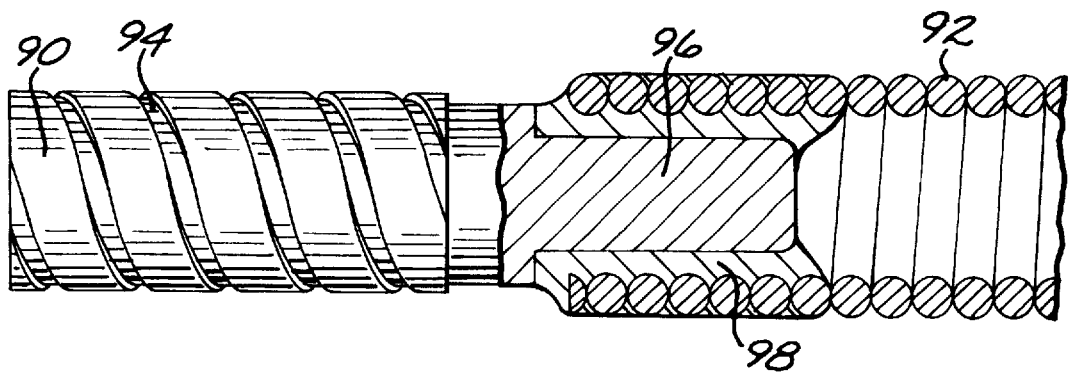
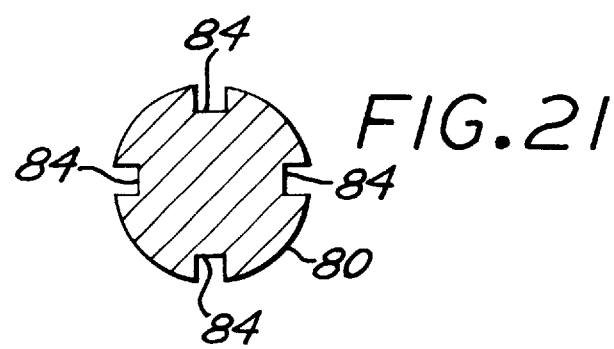
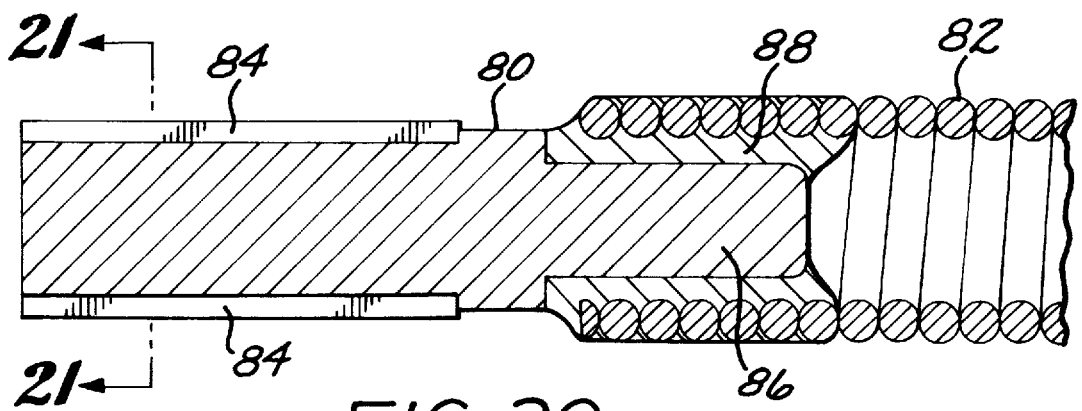

MECHANISM FOR THE DEPLOYMENT OF ENDOVASCULAR IMPLANTS

CROSS-REFERENCE TO RELATED APPLICATIONS

This application is a Continuation-in-Part of application Ser. No. 09/692,248; filed Oct. 18, 2000 now U.S. Pat. No. 6,607,538.

FEDERALLY-SPONSORED RESEARCH OR DEVELOPMENT

Not Applicable

BACKGROUND OF THE INVENTION

This invention relates to the field of methods and devices for the embolization of vascular aneurysms and similar vascular abnormalities. More specifically, the present invention relates to a mechanism for deploying an endovascular implant, such as a microcoil, into a targeted vascular site, and releasing or detaching the implant in the site.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637—Dormandy, Jr. et al., for example, describes a vascular embolization system that employs a detachable balloon delivered to the aneurysm site by an intravascular catheter. The balloon is carried into the aneurysm at the tip of the catheter, and it is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene vinyl alcohol dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Pat. Nos. 4,551,132—Pásztor et al.; 4,795,741—Leshchiner et al.; 5,525,334—Ito et al.; and 5,580,568—Greff et al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic filaments, or filamentous embolic implants. One type of filamentous implant is the so-called "microcoil". Microcoils may be made of a biocompatible metal alloy (typically platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. Pat. Nos. 4,994,069—Ritchart et al.; 5,133,731—Butler et al.; 5,226,911—Chee et al.; 5,312,415—Palermo; 5,382,259—Phelps et al.; 5,382,260—Dormandy, Jr. et al.; 5,476,472—Dormandy, Jr. et al.; 5,578,074—Mirigian; 5,582,619—Ken; 5,624,461—Mariant; 5,645,558—Horton; 5,658,308—Snyder; and 5,718,711—Berenstein et al.

The microcoil approach has met with some success in treating small aneurysms with narrow necks, but the coil must be tightly packed into the aneurysm to avoid shifting that can lead to recanalization. Microcoils have been less successful in the treatment of larger aneurysms, especially those with relatively wide necks. A disadvantage of microcoils is that they are not easily retrievable; if a coil migrates out of the aneurysm, a second procedure to retrieve it and move it back into place is necessary. Furthermore, complete packing of an aneurysm using microcoils can be difficult to achieve in practice.

A specific type of microcoil that has achieved a measure of success is the Guglielmi Detachable Coil ("GDC"). The GDC employs a platinum wire coil fixed to a stainless steel guidewire by a welded connection. After the coil is placed inside an aneurysm, an electrical current is applied to the guidewire, which oxidizes the weld connection, thereby detaching the coil from the guidewire. The application of the current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

The advantages of the GDC procedure are the ability to withdraw and relocate the coil if it migrates from its desired location, and the enhanced ability to promote the formation of a stable thrombus within the aneurysm. Nevertheless, as in conventional microcoil techniques, the successful use of the GDC procedure has been substantially limited to small aneurysms with narrow necks.

A more recently developed type of filamentous embolic implant is disclosed in U.S. Pat. No. 6,015,424—Rosenbluth et al., assigned to the assignee of the present invention. This type of filamentous embolic implant is controllably transformable from a soft, compliant state to a rigid or semi-rigid state. Specifically, the transformable filamentous implant may include a polymer that is transformable by contact with vascular blood or with injected saline solution, or it may include a metal that is transformable by electrolytic corrosion. One end of the implant is releasably attached to the distal end of an elongate, hollow deployment wire that is insertable through a microcatheter to the target vascular site. The implant and the deployment wire are passed through the microcatheter until the distal end of the deployment wire is located within or adjacent to the target vascular site. At this point, the filamentous implant is detached from the wire. In this device, the distal end of the deployment wire terminates in a cup-like holder that frictionally engages the proximal end of the filamentous implant. To detach the filamentous implant, a fluid (e.g., saline solution) is flowed through the deployment wire and enters the cup-like holder through an opening, thereby pushing the filamentous implant out of the holder by fluid pressure.

While filamentous embolic implants have shown great promise, improvement has been sought in the mechanisms for deploying these devices. In particular, improvements have been sought in the coupling mechanisms by which the embolic implant is detachably attached to a deployment instrument for installation in a target vascular site. Examples of recent developments in this area are described in the following patent publications: U.S. Pat. Nos. 5,814,062—Sepetka et al.; 5,891,130—Palermo et al.; 6,063,100—Diaz et al.; 6,068,644—Lulu et al.; and EP 0 941 703 A1—Cordis Corporation.

There is still a need for further improvements in field of coupling mechanisms for detachably attaching an embolic implant to a deployment instrument. Specifically, there is still a need for a coupling mechanism that provides for a secure attachment of the embolic implant to a deployment instrument during the deployment process, while also allowing for the easy and reliable detachment of the embolic implant once it is properly situated with respect to the target site. It would also be advantageous for such a mechanism to allow improved control of the implant during deployment, and specifically to allow the implant to be easily repositioned before detachment. Furthermore, the coupling mechanism should be adaptable for use with a wide variety of endovascular implants, and it should not add appreciably to their costs.

SUMMARY OF THE INVENTION

Broadly, the present invention is a mechanism for the deployment of a filamentous endovascular device, such as an embolic implant, comprising an elongate, flexible, hollow deployment tube having an open proximal end, and a coupling element attached to the proximal end of the endovascular device. The deployment tube includes a distal section terminating in an open distal end, with a lumen defined between the proximal and distal ends. A retention sleeve is fixed around the distal section and includes a distal extension extending a short distance past the distal end of the deployment tube. The endovascular device is attached to the distal end of the deployment tube during the manufacturing process by fixing the retention sleeve around the coupling element, so that the coupling element is releasably held within the distal extension proximate the distal end of the deployment tube. In use, the deployment tube, with the implant attached to its distal end, is passed intravascularly through a microcatheter to a target vascular site until the endovascular device is fully deployed within the site. To detach the endovascular device from the deployment tube, a biocompatible liquid (such as saline solution) is injected through the lumen of the deployment tube so as to apply pressure to the upstream (interior) side of the coupling element. The coupling element is thus pushed out of the retention sleeve by the fluid pressure of the liquid, thereby detaching the endovascular device from the deployment tube.

The coupling element may be a solid "plug" of polymeric material or metal, or it may be formed of a hydrophilic polymer that softens and becomes somewhat lubricious when contacted by the injected liquid. With the latter type of material, the hydration of the hydrophilic material results in physical changes that reduce the adhesion between the coupling element and the sleeve, thereby facilitating the removal of the coupling element from the sleeve upon the application of liquid pressure. Alternatively, the coupling element can be made principally of a non-hydrophilic material (polymer or metal), coated with a hydrophilic coating.

In a specific preferred embodiment, the retention sleeve is made of polyethylene terephthalate (PET), and the coupling element is made of a hydrogel, such as a polyacrylamide/acrylic acid mixture. In another preferred embodiment, both the retention sleeve and the coupling element are made of a polyolefin. In still another preferred embodiment, the retention sleeve is formed of a fluoropolymer, and the coupling element is formed of a metal. Hydrophilic coatings, such as those disclosed in U.S. Pat. Nos. 5,001,009 and 5,331,027, may be applied to any of the non-hydrophilic coupling elements.

In an alternative embodiment, the retention sleeve is made of a shape memory metal, such as the nickel-titanium alloy known as nitinol. In this alternative embodiment, the coupling element would be made of one of the hydrophilic materials mentioned above, or it may be made of a non-hydrophilic material with a hydrophilic coating.

The deployment tube, in the preferred embodiment, comprises a main section having an open proximal end, a distal section terminating in an open distal end, and a transition section connected between the main and distal sections. A continuous fluid passage lumen is defined between the proximal and distal ends. The distal section is shorter and more flexible than the transition section, and the transition section is shorter and more flexible than the main section. This varying flexibility is achieved by making the main section as a continuous length of flexible, hollow tube, the transition section as a length of hollow, flexible laser-cut ribbon coil, and the distal section as a length of flexible, hollow, helical coil. The sections may be joined together by any suitable means, such as soldering.

Preferably, an air purge passage is provided either through or around the coupling element. The purge passage is dimensioned so that a low viscosity fluid, such as saline solution, is allowed to pass freely through it, but a relatively high viscosity fluid, such as a contrast agent, can pass through it only slowly. Before the deployment tube and the attached implant are introduced intravascularly to the target site, a saline solution is injected under low pressure through the lumen of the deployment tube to displace air from the lumen out through the purge passage. After the implant is located within the target site, a high viscosity contrast agent is injected into the deployment tube lumen to purge the remaining saline solution through the purge passage, but, because the contrast agent cannot pass quickly and freely through the purge passage, it builds up pressure on the proximal surface of the coupling element until the pressure is sufficient to push the coupling element out of the retention sleeve.

Any of the embodiments may employ an anti-airflow mechanism for preventing the inadvertent introduction of air into the vasculature during deployment of the implant. One such mechanism comprises an airtight, compliant membrane sealingly disposed over the distal end of the deployment tube. The membrane is expanded or distended distally in response to the injection of the liquid, thereby forcing the implant out of the retention sleeve.

Another such anti-airflow mechanism comprises an internal stylet disposed axially through the deployment tube. The stylet has a distal outlet opening adjacent the distal end of the deployment tube, and a proximal inlet opening in a fitting attached to the proximal end of the deployment tube. The fitting includes a gas/air venting port in fluid communication with the proximal end of the deployment tube. The gas venting port, in turn, includes a stop-cock valve. In use, the liquid is injected through the stylet with the stop-cock valve open. The injected liquid flows out of the stylet outlet opening and into the deployment tube, hydraulically pushing any entrapped air out of the venting port. When liquid begins flowing out of the venting port, indicating that any entrapped air has been fully purged from the deployment tube, the stop-cock is closed, allowing the continued flow of the liquid to push the implant out of the retention sleeve, as described above.

As will be appreciated more fully from the detailed description below, the present invention provides a secure attachment of the embolic implant to a deployment instrument during the deployment process, while also allowing for the easy and reliable detachment of the embolic implant once it is properly situated with respect to the target site. The present invention also provides improved control of the implant during deployment, and specifically it allows the implant to be easily repositioned before detachment. Furthermore, the present invention is readily adaptable for use with a wide variety of endovascular implants, without adding appreciably to their costs.

BRIEF DESCRIPTION OF THE DRAWINGS

FIG. 1 is an elevational view of an endovascular device deployment mechanism in accordance with a preferred embodiment of the present invention, showing the mechanism with an endovascular implant device attached to it;

FIG. 2 is a longitudinal cross-sectional view of the deployment mechanism and the endovascular implant of FIG. 1, taken along line 2—2 of FIG. 1;

FIG. 3 is a cross-sectional view, similar to that of FIG. 2, showing the first step in separating the implant from the deployment tube of the deployment mechanism;

FIG. 4 is a cross-sectional view, similar to that of FIG. 3, showing the deployment mechanism and the implant after the act of separation;

FIG. 5 is a cross-sectional view of the endovascular implant deployment mechanism incorporating a first type of anti-airflow mechanism;

FIG. 6 is a cross sectional view of the deployment mechanism of FIG. 5, showing the mechanism with an endovascular implant device attached to it;

FIG. 7 is a cross-sectional view, similar to that of FIG. 6, showing the implant in the process of deployment;

FIG. 8 is a cross-sectional view, similar to that of FIG. 7, showing deployment device after the implant has been deployed;

FIG. 9 is an elevational view of the endovascular implant deployment device incorporating a second type of anti-airflow mechanism, showing the device with an implant attached to it;

FIG. 10 is a cross-sectional view of the distal portion of the deployment device of FIG. 9 and the proximal portion of the implant, taken along line 10—10 of FIG. 9;

FIG. 13 is an elevational view of an endovascular implant deployment device in accordance with a modified form of the preferred embodiment of the invention, showing the device with an implant attached to it; FIG. 14 is a cross-sectional view taken along line 14—14 of FIG. 13;

FIGS. 15–17 are cross-sectional views, similar to that of FIG. 14, showing the process of deploying the implant;

FIG. 18 is a cross-sectional view of the endovascular implant deployment device incorporating a modified form of the first type of anti-airflow mechanism, showing the device with an implant attached to it;

FIG. 19 is a cross-sectional view, similar to that of FIG. 18, showing the implant in the process of deployment;

FIG. 20 is an axial cross-sectional view of the distal end of a deployment device and the proximal end of an implant in accordance with the present invention, showing a modified form of the coupling element with a peripheral air purge passage;

FIG. 21 is a cross-sectional view taken along line 21—21 of FIG. 20; and

FIG. 22 is an elevational view, partially in axial cross-section, of the distal end of a deployment device and the proximal end of an implant in accordance with the present invention, showing another modified form of a coupling element with a peripheral air purge passage.

DETAILED DESCRIPTION OF THE INVENTION

Figure 11:
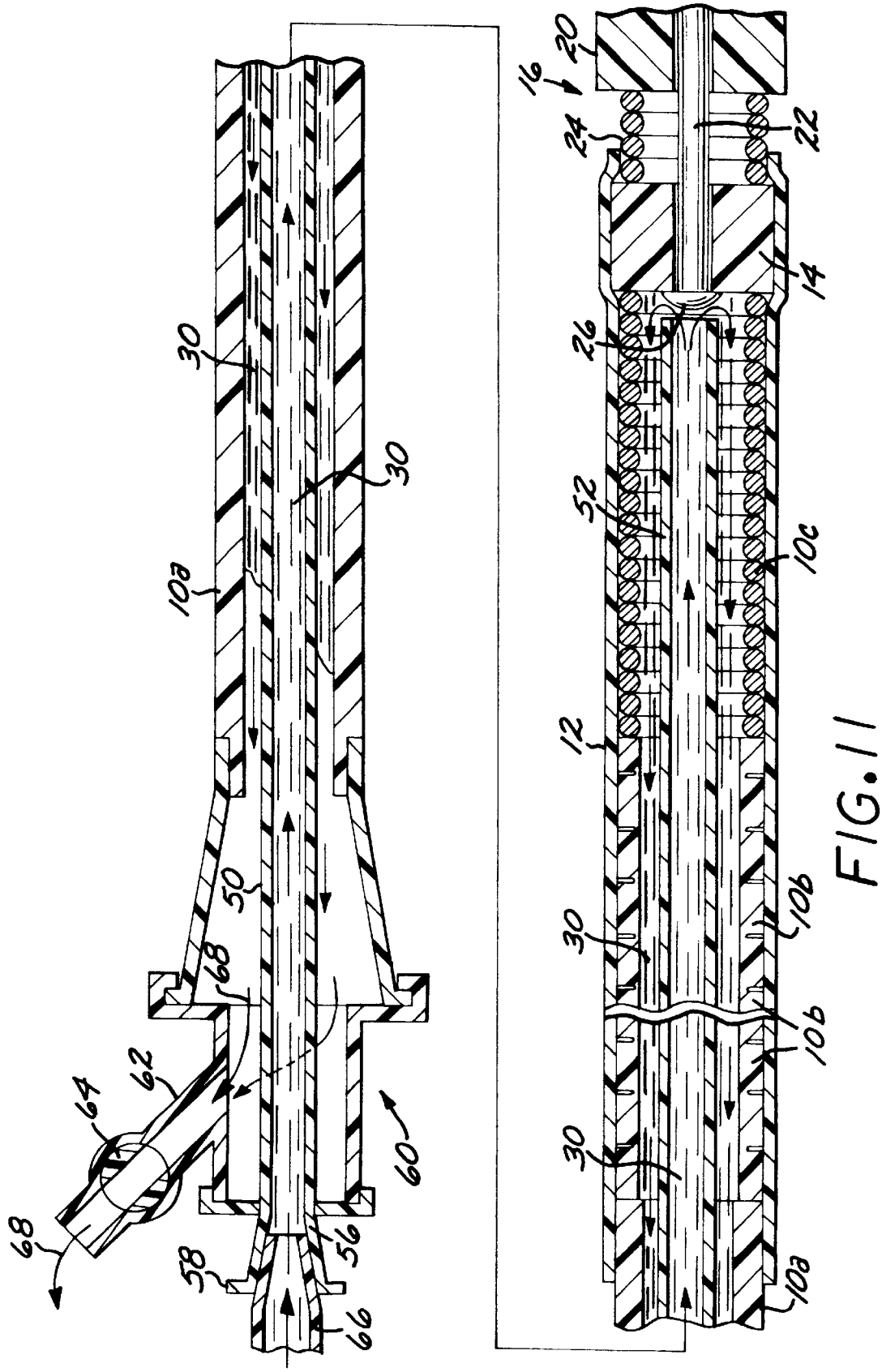
FIG. 11 is a cross-sectional view of the deployment device and the attached implant.

Referring first to FIG. 1, a deployment mechanism for an endovascular device, in accordance with the present invention, comprises an elongate, flexible, hollow deployment tube 10 having an open proximal end 11 (see FIG. 11) and a distal section terminating in an open distal end 13, with a continuous fluid passage lumen 15 defined between the proximal and distal ends. A retention sleeve 12 is fixed around the distal section of the deployment tube 10, and it includes a distal extension 17 extending a short distance past the distal end 13 of the deployment tube. The deployment mechanism further comprises a coupling element 14 fixed to the proximal end of a filamentous endovascular device 16 (only the proximal portion of which is shown), which may, for example, be an embolic implant.

The deployment tube 10 is made of stainless steel, and it is preferably formed in three sections, each of which is dimensioned to pass through a typical microcatheter. A proximal or main section 10a is the longest section, about 1.3 to 1.5 meters in length. The main section 10a is formed as a continuous length of flexible, hollow tubing having a solid wall of uniform inside and outside diameters. In a specific preferred embodiment, the inside diameter is about 0.179 mm, and the outside diameter is about 0.333 mm. An intermediate or transition section 10b is soldered to the distal end of the main section 10a, and is formed as a length of hollow, flexible laser-cut ribbon coil. In a specific preferred embodiment, the transition section 10b has a length of about 300 mm, an inside diameter of about 0.179 mm, and an outside diameter of about 0.279 mm. A distal section 10c is soldered to the distal end of the transition section 10b, and is formed as a length of flexible, hollow helical coil. In a specific preferred embodiment, the distal section 10c has a length of about 30 mm, an inside diameter of about 0.179 mm, and an outside diameter of about 0.253 mm. A radiopaque marker (not shown) may optionally be placed about 30 mm proximal from the distal end of the distal section 10c. It will be appreciated that the transition section 10b will be more flexible than the main section 10a, and that the distal section 10c will be more flexible than the transition section 10b.

The coupling element 14 is fastened to the proximal end of the endovascular device 16. The endovascular device 16 is advantageously of the type disclosed and claimed in co-pending application Ser. No. 09/410,970, assigned to the assignee of the present invention, although the invention can readily be adapted to other types of endovascular devices. Specifically, the endovascular device 16 is an embolization device that comprises a plurality of biocompatible, highly-expansible, hydrophilic embolizing elements 20 (only one of which is shown in the drawings), disposed at spaced intervals along a filamentous carrier 22 in the form of a suitable length of a very thin, highly flexible filament of nickel/titanium alloy. The embolizing elements 20 are separated from each other on the carrier by radiopaque spacers in the form of highly flexible microcoils 24 (only one of which is shown in the drawings) made of platinum or platinum/tungsten alloy, as in the thrombogenic microcoils of the prior art, as described above. In a preferred embodiment, the embolizing elements 20 are made of a hydrophilic, macroporous, polymeric, hydrogel foam material, in particular a water-swellable foam matrix formed as a macroporous solid comprising a foam stabilizing agent and a polymer or copolymer of a free radical polymerizable hydrophilic olefin monomer cross-linked with up to about 10% by weight of a multiolefin-functional crosslinking agent. Such a material is described in U.S. Pat. No. 5,750,585—Park et al., the disclosure of which is incorporated herein by reference. The material may be modified, or provided with additives, to make the implant visible by conventional imaging techniques.

The endovascular device 16 is modified by extending the filamentous carrier 22 proximally so that it provides an attachment site for the coupling element 14 at the proximal end of the carrier 22. A sealing retainer 26 terminates the proximal end of the carrier 22, providing a sealing engagement against the distal end of the coupling element 14.

The coupling element 14 is removably attached to the distal end of the deployment tube by the retention sleeve 12, which is secured to the deployment tube 10 by a suitable adhesive or by solder (preferably gold-tin solder). The retention sleeve 12 advantageously covers the transition section 10b and the distal section 10c of the deployment tube, and its proximal end is attached to the distal end of the main section 10a of the deployment tube 10. The retention sleeve 12 has a distal portion that extends distally past the distal end of the deployment tube 10 and surrounds and encloses the coupling element 14. The coupling element 14 has an outside diameter that is greater than the normal or relaxed inside diameter of the retention sleeve 12, so that the coupling element 14 is retained within the retention sleeve 12 by friction and/or the radially inwardly-directed polymeric forces applied by the retention sleeve 12.

The coupling element 14 may be a solid "plug" of polymeric material or metal, or it may be formed of a hydrophilic polymer that softens and becomes somewhat lubricious when contacted by a hydrating liquid, as discussed below. With the latter type of material, the hydration of the hydrophilic material results in physical changes that reduce the frictional adhesion between the coupling element 14 and the sleeve 12, thereby facilitating the removal of the coupling element 14 from the sleeve 12 upon the application of liquid pressure to the upstream (proximal) side of the coupling element 14, as will be described below. Alternatively, the coupling element 14 can be made principally of a non-hydrophilic material (polymer or metal), and coated with a hydrophilic coating.

In a first preferred embodiment, the retention sleeve 12 is made of polyethylene terephthalate (PET) or polyimide, and the coupling element 14 is made either of a metal (preferably platinum) or of a hydrogel, such as a polyacrylamide/acrylic acid mixture. In another preferred embodiment, both the retention sleeve 12 and the coupling element 14 are made of a polyolefin. In still another preferred embodiment, the retention sleeve 12 is formed of a fluoropolymer, and the coupling element 14 is formed of a metal. Hydrophilic coatings, such as those disclosed in U.S. Pat. Nos. 5,001,009 and 5,331,027 (the disclosures of which are incorporated herein by reference), may be applied to any of the non-hydrophilic coupling elements 14. In these embodiments, the retention sleeve 12 may be formed as a "shrink tube" that is fitted over the coupling element 14 and then shrunk in place by the application of heat to secure the coupling element in place. The heat shrinking process semi-crystallizes the polymeric chains so that sleeve is somewhat stiffened and made resistant to radial expansion (although still expansible axially). Alternatively, the retention sleeve 12 may be made of an elastic polymer that is stretched to receive the coupling element 14, and then retains the coupling element 14 by the resulting elastomeric forces that are directed radially inwardly.

In an alternative embodiment, the retention sleeve 12 is made of a shape memory metal, such as the nickel-titanium alloy known as nitinol. In this alternative embodiment, the coupling element 14 would be made of one of the hydrophilic materials mentioned above, or it may be made of a non-hydrophilic material with a hydrophilic coating. In this embodiment, the retention sleeve 12 is radially stretched to receive the coupling element 14, and it retains the coupling element 14 by the forces resulting from the tendency of the shape memory metal to return to its original configuration.

Use of the deployment mechanism of the present invention is illustrated in FIGS. 3 and 4. The endovascular device 16 and the deployment tube 10 are passed intravascularly through the lumen of a microcatheter (not shown) until the endovascular device 16 is situated in a targeted vascular site, such as an aneurysm. A suitable liquid 30, such as saline solution, is then injected into the interior of the deployment tube, under pressure, as show in FIG. 3. The pressure of the liquid against the upstream side of the coupling element pushes the coupling element 14 out of the retention sleeve 12 to separate the endovascular device 16 from the deployment tube, as shown in FIG. 4. While a polymer retention sleeve may deform in the axial direction during the separation process, it does not substantially expand in the radial direction. (A metal retention sleeve would not undergo any significant deformation.) If the coupling element 14 is made of a hydrophilic material, or if it has a hydrophilic coating, the physical changes in the coupling element 14 due to the hydrophilic properties of the coupling element 14 or its coating, as described above, will facilitate the separation process. The deployment tube 10 and the microcatheter are then withdrawn.

It will be appreciated that, until the liquid 30 is injected, the deployment tube 10 can be manipulated to shift the position of the endovascular device 16, which will stay attached to the deployment tube 10 during the manipulation. Thus, repositioning of the endovascular device 16 is facilitated, thereby providing better placement of the device 16 within the targeted site.

In many instances, it will be desired to take special precautions against the introduction of air into the vasculature. Accordingly, the present invention may be adapted to incorporate an anti-airflow mechanism. A first type of anti-airflow mechanism, illustrated in FIGS. 5–8, comprises a flexible, expansible, compliant membrane 40, preferably of silicone rubber, sealingly disposed over the distal end of the deployment tube 10. The distal end of the deployment tube 10 is covered by a thin, flexible, polymeric sheath 42, and the membrane 40 is attached to the sheath 42 by a suitable biocompatible adhesive, such as cyanoacrylate. As shown in FIG. 6, the endovascular device 16 is attached to the deployment tube 10 by means of the retention sleeve 12 and the coupling element 14, as described above, with the membrane 40 disposed between the distal end of the deployment tube 10 and the proximal end of the coupling element 14.

In use, as shown in FIGS. 7 and 8, the liquid 30 is injected into the deployment tube, as described above. Instead of directly impacting the coupling element 14, however, it expands the membrane 40 distally from the distal end of the deployment tube 10 (FIG. 7), thereby pushing the coupling element 14 out of the retention sleeve to deploy the endovascular device 16. After the deployment, the membrane resiliently returns to its original position (FIG. 8). Thus, the injected liquid 30 is completely contained in a closed system, and any air that may be entrapped in the deployment tube 10 is prevented from entering the vasculature by the airtight barrier present by the membrane 40.

FIGS. 9–12 illustrate a second type of anti-airflow mechanism that may be used with the present invention. This second type of anti-airflow mechanism comprises an internal stylet 50 disposed axially through the deployment tube 10. The stylet 50 has a flexible distal portion 52 terminating in an outlet opening 54 adjacent the distal end of the deployment tube 10, and a proximal inlet opening 56 that communicates with an inlet port 58 in a fitting 60 attached to the proximal end of the deployment tube. The fitting 60 includes a gas venting port 62 in fluid communication with the proximal end of the deployment tube. The gas venting port 62, in turn, includes a stop-cock valve 64.

Figure 12:
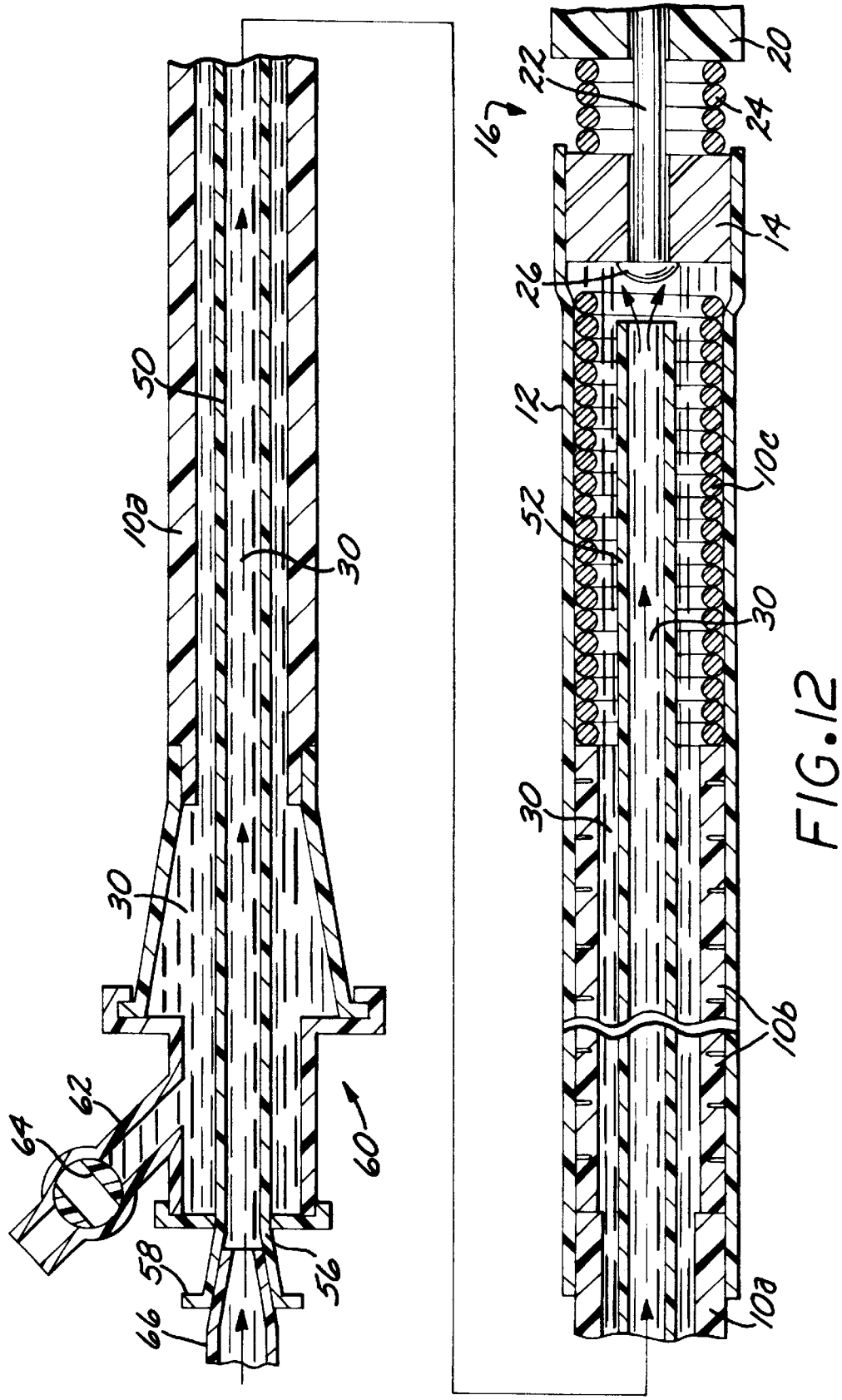
FIG. 12 is a cross-sectional view, similar to that of FIG. 11, showing the implant in the process of deployment.

The operation of the second type of anti-airflow mechanism during deployment of the endovascular device 16 is shown in FIGS. 11 and 12. As shown in FIG. 11, with the stop-cock valve 64 open, the liquid 30 is injected into the stylet 50 through the inlet port 58 by means such as a syringe 66. The injected liquid 30 flows through the stylet 50 and out of the stylet outlet opening 54 and into the deployment tube 10, hydraulically pushing any entrapped air (indicated by arrows 68 in FIG. 11) out of the venting port 62. When the liquid 30 begins flowing out of the venting port 62, indicating that any entrapped air has been fully purged from the deployment tube 10, the stop-cock valve 64 is closed (as shown in FIG. 12), allowing the continued flow of the liquid 30 to push the endovascular device 16 out of the retention sleeve 12, as described above.

FIGS. 13–17 illustrate a modification of the preferred embodiment of the invention that facilitates the performance of an air purging step before the deployment tube and the endovascular device are intravascularly passed to the target site. This modification includes a modified coupling element 14' having an axial air purge passage 72 through its interior. The purge passage 72 is provided through a central coupling element portion 74 contained within an inner microcoil segment 76 located coaxially within the coupling element 14'. The diameter of the purge passage 72 is preferably between about 0.010 mm and about 0.025 mm, for the purpose to be described below.

A detachment zone indicator sleeve 70, attached to the distal extension 17 of the retention sleeve 12 by a bond joint 71, is disposed coaxially around a proximal portion (approximately one-half) of the distal extension 17 of the retention sleeve 12, leaving approximately the distal half of the distal extension 17 exposed. The detachment zone indicator sleeve 70 thus overlaps the juncture between the coupling element 14' and the distal end of the deployment tube 10, and reinforces the retention sleeve 12 at this juncture against the stresses resulting from the bending of the assembly as it is passed intravascularly to the target vascular site. Furthermore, the detachment zone indicator sleeve 70 restrains the retention sleeve 70 from radial expansion. The detachment zone indicator sleeve 70 may be made of polyimide or platinum. If made of polyimide, its color is advantageously one that contrasts with the color of the retention sleeve 12, so that the detachment zone (i.e., the juncture between the coupling element 14' and the deployment tube 10) can be easily visualized before the intravascular deployment. If made of platinum, the detachment zone can be visualized within the body by X-ray or other conventional visualization methods.

As shown in FIG. 15, before the deployment tube 10 and the endovascular device are introduced intravascularly, as described above, saline solution 30 is injected into the lumen 15 to purge air from the mechanism. The purged air exits through the purge passage, as indicated by the arrows 78 in FIG. 15, and out the distal end (not shown) of the endovascular device. It may be advantageous to place the distal end of the endovascular device in a receptacle of sterile saline solution, so that the cessation of air bubbles may be noted, indicating a complete purging of air. The saline is injected at a sufficiently low pressure (such as by use of a 3 cc syringe), that the coupling element 14' is not pushed out of the retention sleeve 12. Some of the saline solution 30 also is purged through the purge passage 72, the diameter of which is sufficiently large to allow the relatively free flow of the saline solution 30 through it.

Figure 16:
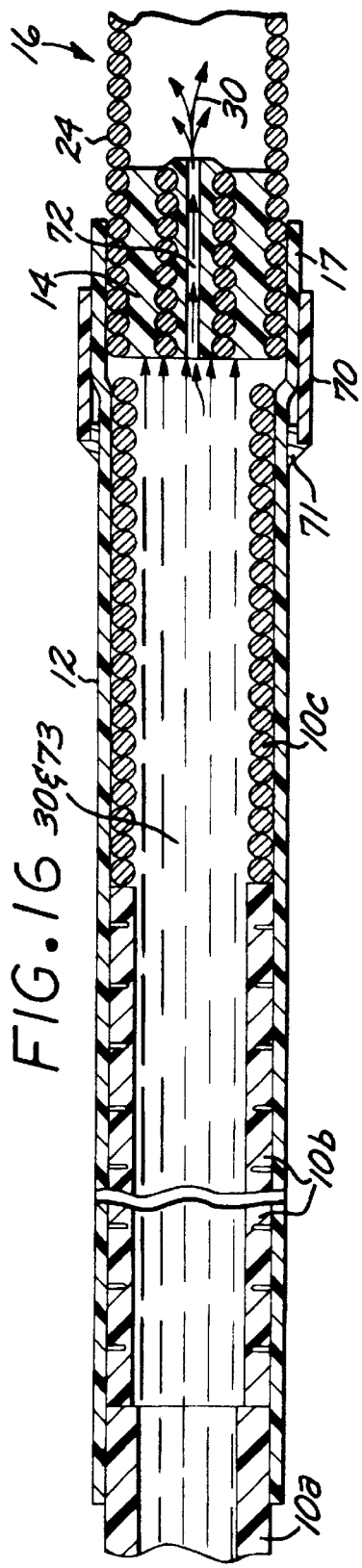
Figure 17:
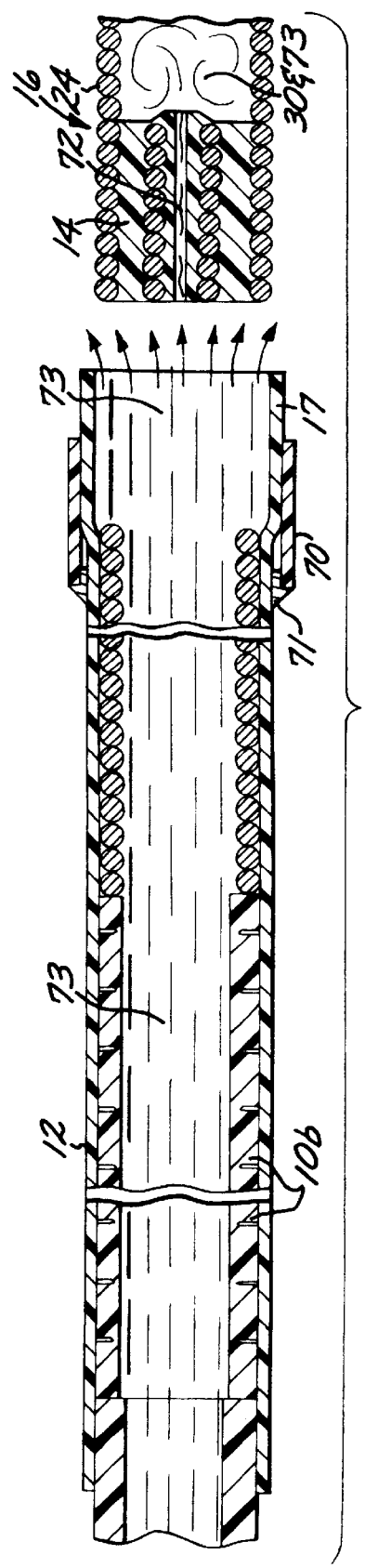

After the endovascular device has been located in the target vascular site, as described above, a contrast agent 73 is injected into the lumen 15, as shown in FIG. 16. The contrast agent 73 has a much higher viscosity than the saline solution 30 (2–10 cP vs. approximately 1 cP). Therefore, the contrast agent 73 pushes the remaining saline solution 30 out through the purge passage 72. Because of the relatively high viscosity of the contrast agent 73 and the relatively small diameter of the purge passage 72, the purge passage 72 restricts (but does not completely block) the flow of the contrast agent 73 through it; thus, the contrast agent 73 does not pass quickly or easily through the purge passage 72. As the contrast agent 73 continues to flow into the lumen 15, pressure builds up on the proximate side of the coupling element 14', until it is pushed out of the retention sleeve 12, as shown in FIG. 17.

Alternatively, detachment of the endovascular device can be achieved by injecting saline solution at a high enough pressure or flow rate to push the coupling element 14' of the retention sleeve 12, notwithstanding the flow of the saline solution through the purge passage 72.

A modified form of the first type of anti-airflow mechanism is shown in FIGS. 18 and 19. This modification comprises a flexible, but non-compliant barrier in the form of a non-compliant membrane 40', preferably of PET, sealingly disposed over the distal end of the deployment tube 10. The distal end of the deployment tube 10 is covered by a thin, flexible, polymeric sheath 42', and the membrane 40' is attached to the sheath 42' by a suitable biocompatible adhesive, such as cyanoacrylate. As shown in FIG. 18, the membrane 40' is shaped so that it normally assumes a first or relaxed position, in which its central portion extends proximally into the lumen 15 of the deployment tube 10. The endovascular device 16 is attached to the deployment tube 10 by means of a frictional fit between the membrane 40' and the coupling element 14, the former forming a tight-fitting receptacle for the latter. The retention may be enhanced by a suitable adhesive (e.g., cyanoacrylate). The coupling element 14 is thus contained within lumen 15 near the distal end of the deployment tube 10.

FIG. 19 shows the use of the modified form of the first type of anti-airflow device in the deployment of the endovascular device 16. As described above, the liquid 30 is injected into the deployment tube 10, pushing the membrane 40' distally from the distal end toward a second or extended position, in which projects distally from the distal end of the deployment tube 10. As the membrane 40' is pushed toward its extended position, it pushes the coupling element 14 out of the distal end of the deployment tube 10 to deploy the endovascular device 16. Thus, the injected liquid 30 is completely contained in a closed system, and any air that may be entrapped in the deployment tube 10 is prevented from entering the vasculature by the airtight barrier present by the membrane 40'.

FIGS. 20 and 21 show a modified coupling element 80 attached to the proximal end of an endovascular implant 82, similar to any of the previously described implants. The coupling element 80 is preferably formed of one of the metals described above (preferably platinum), or it may be made of a suitable polymer (as described above). It is configured as a substantially cylindrical member having at least one, and preferably several, longitudinal flutes or grooves 84 extending along its exterior periphery for most of its length. Although four such grooves or flutes 84 are shown, as few as one such groove or flute may be employed, or as many as six or more. Each of the grooves or flutes 84 forms a peripheral air purge passage along the exterior surface of the coupling element 80; that is, between the exterior surface of the coupling element 80 and the retention sleeve (described above but not shown in these figures).

The coupling element 80 terminates in an integral, substantially cylindrical distal extension or plug 86 of reduced diameter. The distal plug 86 is inserted into the proximal end of the implant 82 and attached to it by a suitable biocompatible bonding agent or adhesive 88. Alternatively, if the coupling element is made of metal, the attachment may be by soldering or welding.

FIG. 22 illustrates a device having another modified coupling element 90 attached to the proximal end of an implant 92. This coupling element 90 may also be made of one of the above-described metals (preferably platinum), or one of the above-described polymers. It is configured as a substantially cylindrical member having a helical groove or flute 94 formed in its exterior surface. The flute or groove 94 forms a peripheral air purge passage along the exterior surface of the coupling element 90, as do the longitudinal flutes or grooves of the embodiment of FIGS. 20 and 21. The coupling element 90 includes an integral distal extension or plug 96, of reduced diameter, that is inserted into the proximal end of the implant 92 and attached to it by means of a suitable biocompatible bonding agent 98 (e.g., solder or adhesive) or by welding, depending on the material of which the coupling element 90 is made.

The longitudinal flutes or grooves 84 (in the coupling element 80) and helical flute or groove 94 (in the coupling element 90) provide fluid passages for purging air and saline solution, as does the internal axial passage 72 in the embodiment described above and shown in FIGS. 13–17. Accordingly, for this purpose, the flutes or grooves 84, 94 are dimensioned to allow the free passage of a low viscosity fluid (such as saline solution), while allowing only a relatively slow passage of a relatively high viscosity fluid (such as a typical contrast agent). Thus, as described above, the pressure on the upstream side of the coupling element is allowed to build up when the contrast agent is injected until the coupling element is dislodged from the retention sleeve. Alternatively, a low viscosity fluid, such as saline solution, may be injected at a sufficiently high flow rate or pressure to push the coupling element out of the retention sleeve, notwithstanding the flow of the saline solution through the purge passage.

Furthermore, the fluted or grooved surface of the coupling elements 80, 90 enhances the frictional engagement between the coupling element and the retention sleeve. To provide even further enhancement of this frictional engagement, the surface of the coupling element and/or the interior surface of the retention sleeve may be treated with a suitable biocompatible coating or surface treatment (as will be known to those skilled in the pertinent arts), or the coupling element may be formed with a micro-textured surface, in accordance with known techniques.

It will thus be appreciated that the present invention provides a coupling mechanism that yields a secure attachment of the endovascular device to a deployment instrument during the deployment process, while also allowing for the easy and reliable detachment of the endovascular device once it is properly situated with respect to the target site. The coupling mechanism of the present invention also provides improved control of the endovascular device during deployment, and specifically it allows the endovascular device to be easily repositioned before detachment. In addition, the coupling mechanism of the present invention advantageously includes an effective mechanism for precluding airflow into the vasculature during the deployment process. Furthermore, the coupling mechanism of the present invention is readily adaptable for use with a wide variety of endovascular devices, without adding appreciably to their costs.

Although a number of specific embodiments are described above, it should be appreciated that these embodiments are exemplary only, particularly in terms of materials and dimensions. For example, many suitable materials for both the coupling element 14 and the retention sleeve 12 may be found that will yield satisfactory performance in particular applications. Also, the exemplary dimensions given above may be changed to suit different specific clinical needs. These modifications and others that may suggest themselves to those skilled in the pertinent arts are deemed to be within the spirit and scope of the present invention, as defined in the claims that follow.

What is claimed is:

1. A deployment mechanism for deploying a filamentous endovascular device having a proximal end, comprising:
    an elongate, flexible, hollow deployment tube having an open proximal end, a distal section terminating in an open distal end, and a lumen defined between the proximal and distal ends;

a retention sleeve fixed around the distal section of the deployment tube and having a distal extension extending a short distance past the distal end of the deployment tube; and a coupling element attached to the proximal end of the endovascular device and releasably held within the distal extension of the retention sleeve proximate the distal end of the deployment tube so as to be displaceable from the retention sleeve in response to fluid pressure applied to the coupling element through the lumen and the distal end of the deployment tube;

wherein the coupling element is formed with a purge passage that is dimensioned so as to provide a substantial restriction to the flow therethrough of a fluid having a viscosity that is substantially greater than that of saline solution.

2. The deployment mechanism of claim 1, wherein the coupling element is formed from a non-hydrophilic material.

3. The deployment mechanism of claim 2, wherein the retention sleeve is made of a fluorocarbon and the coupling element is made of metal.

4. The deployment mechanism of claim 1, wherein the purge passage passes through the interior of the coupling element.

5. The deployment mechanism of claim 1, wherein coupling element has an exterior periphery, and wherein the purge passage is located on the exterior periphery of the coupling element.

6. The deployment mechanism of claim 5, wherein the purge passage extends longitudinally along the exterior periphery of the coupling element.

7. The deployment mechanism of claim 6, wherein the purge passage is a first purge passage, and wherein the coupling element is formed with at least a second purge passage extending longitudinally along the exterior periphery of the coupling element.

8. The deployment mechanism of claim 5, wherein the purge passage is helical.

9. The deployment mechanism of claim 1, wherein the purge passage is dimensioned to provide a substantial restriction to the flow therethrough of a fluid having a viscosity greater than or approximately equal to 2 cP.

10. A method of deploying a filamentous endovascular device into a target vascular site, comprising the steps of:

(a) providing a filamentous endovascular device having a proximate end releasably coupled to an elongate, flexible, hollow deployment tube having an open proximal end, a distal section terminating in an open distal end, and a lumen defined between the proximal and distal ends, the endovascular device having a coupling element releasably attached to the deployment tube adjacent the open distal end thereof, the coupling element being formed with a purge passage that is dimensioned so as to provide a substantial restriction to the flow therethrough of a fluid having a viscosity substantially greater than that of saline solution;

(b) purging air from the lumen by injecting saline solution through the lumen with a pressure sufficient to displace air from the lumen through the purge passage but not sufficient to separate the endovascular device from the deployment tube;

(c) introducing the endovascular device intravascularly to the target vascular site while it is attached to the deployment tube; and (d) injecting a liquid through the lumen under sufficient pressure to separate the endovascular device from the deployment tube in response to the liquid pressure applied to the coupling element through the open distal end of the deployment tube.

11. The method of claim 10, wherein the injecting step comprises the step of injecting a relatively high viscosity liquid through the lumen with a pressure sufficient to displace the saline solution from the lumen through the purge passage and to separate the endovascular device from the deployment tube.

12. The method of claim 11, wherein the relatively high viscosity liquid is a contrast agent having a viscosity of at least about 2 cP.

13. The method of claim 10, wherein the coupling element is releasably held by a retention sleeve fixed to the distal section of the deployment tube.

14. The method of claim 13, wherein the retention sleeve is not substantially expanded in the radial direction during the injection step.

15. The method of claim 10, wherein the injected liquid in the injecting step applies pressure directly to the coupling element.

16. The method of claim 10, wherein the purge passage extends through the interior of the coupling element.

17. The method of claim 10, wherein coupling element has an exterior periphery, and wherein the purge passage is located on the exterior periphery of the coupling element.

18. The method of claim 17, wherein the purge passage extends longitudinally along the exterior periphery of the coupling element.

19. The method of claim 18, wherein the purge passage is a first purge passage, and wherein the coupling element is formed with at least a second purge passage extending longitudinally along the exterior periphery of the coupling element.

20. The method claim 17, wherein the purge passage is helical.

* * * * *